(12) United States Patent
Himbert et al.

(10) Patent No.: US 6,238,371 B1
(45) Date of Patent: May 29, 2001

(54) DEVICE FOR ACCLIMATIZATION TO THERAPY BY INJECTIONS

(75) Inventors: Hans Himbert, Bromma; Carl-Göran Crafoord, Djursholm, both of (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 08/817,123

(22) PCT Filed: Oct. 9, 1995

(86) PCT No.: PCT/SE95/01159

§ 371 Date: Apr. 8, 1997

§ 102(e) Date: Apr. 8, 1997

(87) PCT Pub. No.: WO96/11026

PCT Pub. Date: Apr. 18, 1996

(30) Foreign Application Priority Data

Oct. 10, 1994 (SE) .................................... 9403433

(51) Int. Cl.[7] .................................... A61M 5/00
(52) U.S. Cl. .................... 604/187; 604/192; 604/263
(58) Field of Search .................... 604/198, 192, 604/187, 263, 110

(56) References Cited

U.S. PATENT DOCUMENTS

| | | |
|---|---|---|
| 4,725,267 | 2/1988 | Vaillancourt . |
| 4,775,369 | 10/1988 | Schwartz . |
| 4,968,299 | 11/1990 | Ahlstrand et al. . |
| 5,417,662 | 5/1995 | Hjertman et al. . |

FOREIGN PATENT DOCUMENTS

| | | |
|---|---|---|
| 42 01 228 | 1/1992 | (DE) . |
| 399181 | 2/1978 | (SE) . |
| 406708 | 2/1979 | (SE) . |
| WO 91/16935 | 4/1991 | (WO) . |
| WO 93/24162 | 12/1993 | (WO) . |

*Primary Examiner*—J. Yasko
(74) *Attorney, Agent, or Firm*—Gilberto M. Villacorta; Corinne M. Pouliquen; Pepper Hamilton L.L.P.

(57) ABSTRACT

The present invention is directed to a cannula, attachable to an injection device comprising a needle entirely surrounded by an essentially cylindrical collapsible needle cover in order to visually hide the entire needle during the whole procedure of administration by injection. The collapsible needle cover comprises a resilient, cylindrical or vaguely conical sleeve made of a foamed polymer and is provided with an axially extended hole for the needle, alternatively the needle cover can have a bellows-like structure. Also disclosed is a method of administering a medicament by injection with needle hidden from visual impression during the whole administration process.

29 Claims, 1 Drawing Sheet

DEVICE FOR ACCLIMATIZATION TO THERAPY BY INJECTIONS

FIELD OF INVENTION

The present invention is directed to a cannula comprising a collapsible needle cover to hide the needle from visual impression, while being able to use substantially the whole length of the needle for injective penetration, and also a method of injection of injection employing such a cannula attached to a conventional injection device. The invention is particularly useful for the acclimatization of a patient to a long term regimen of administration of a drug by means of injection.

BACKGROUND OF THE INVENTION

It is highly desirable to obtain convenient administration forms in medical therapy with drugs that must be administered by injections during long periods, often by self-administration in the home of the patient. Examples of such drugs are sensitive human proteins like insulin and human growth hormone which so far only can be administered by injections with therapeutical efficacy. Many patients who must be confined to such long term regimens are, however, severely discomforted by the constant use of needles and they frequently feel strong aversions to the visual appearance of a needle and the subsequent predicted pain sensation. In particular, many infant patients in the need of regular growth hormone injections might require devices that visually hides the needle during the entire administration procedure to overcome the inconvenience of the therapy. Especially, since the growth hormone injections, in contrast to e.g. insulin therapy for diabetes, is not linked to a direct alleviation of symptoms, growth hormone patients would benefit considerably from a device that can provide an acclimatization period to an initially uncomfortable therapy by means of injections.

In the International patent application WO 93/05835, a needle protecting device is disclosed comprising a displaceable tubular sleeve which in its extended position completely surrounds the injection needle. Such an arrangement is however, complicated in structure and therefore expensive, and might be difficult to use for children, since it requires that the user overcomes the forces of a spring device for injection. It must also be disengaged from the body of the pen-formed syringe and be remounted thereto after each change of needle or cannula which can be experienced as troublesome and in worst case might lead to an improper performance.

A resilient needle protecting device, for example in the form of a tubular bellows, is disclosed by the German patent application DE 42 01 228. This device is arranged with an attached movable stop surface with a hole for the needle. It requires an additional movement for readying needle for injection. The attached stop surface also leads to that a certain part of the needle will not be used in injection. The International patent application WO 93/24162 discloses a protective sheath member slidably disposed over the cannula. This construction also requires a manual movement of the sheath, in order to move it away from the distal end of the cannula, so that the needle is exposed for injection. The sheath member will provide a protection from accidental needle sticks for normal users, but it will not visually hide the needle during the whole injection performance and it will not make use of the entire needle length for injection. The International patent application WO 91/16935 discloses a needle shield of made of an axially retractable, resilient material having a transparent tip section with an axially offset position to prevent accidental exposure of the needle tip, both before and after injection The device must be tilted in a predetermined manner to expose the needle for injection and is not intended to hide the needle for the user.

The above-mentioned constructions all require a considerable skill to ready for the injection, because the needle cover must be adjusted in a given manner to expose the needle. There is also considerable risk that the needle cover unintentionally will be penetrated so the needle sterility is lost and that splinters torn away from the cover material might be introduced in the body with the injection.

Moreover, the US patent 4,775,369 discloses a needle shield of a foamed resilient material which is compressed against the site of injection to expose the needle. The front end device is, however, provided with an incompressible tubular guide portion that leaves a considerable part of the needle unused for penetration. The guide portion will also unable the user to make such a slight unintentional tilt of the injection device and needle, as often being made by inexperienced patients. The needle shield according to U.S. Pat. No. 4,775,369 will also accustom the patient to a certain penetration depth which is a bit shorter than without the needle shield. It will lead to that the injection conditions will not be identically the same, if the injection device for some reason is used without the habitual needle shield. A non-identical injection situation, due to a changed injection depth, can lead to that the patients feel more pain than usual or, in worst case, that the patient obtains a varied effect of the drug. A reproducible injection depth is especially desirable in applications where subcutaneous injections, instead of intramuscular injections, are preferred.

All the mentioned drawbacks of needle covers belonging to the prior art will also become more pronounced when infants shall use the injection device for self-injection, especially during an initial acclimatization period.

It is the object of the present invention to provide a simple and cheap needle hiding construction to be used with conventional injection devices, such as syringes and injection pens.

Another object of the present invention is to efficiently hide the needle for the user during the entire administration procedure, while providing identical injection condition regardless if needle hiding construction is used or not.

It is also the object of the present invention to provide for a manually simple repeatable and convenient injection by using standardized needles and cannulas and to avoid excessively long needles that might lead to a uncomfortable high flow resistance during the injection.

A further object of the present invention is to eliminate all unnecessary manual operations to perform the injection.

These objects are attained by the cannula according to claim 1 and by method of administering a medicament according to claim 6.

DESCRIPTION OF THE INVENTION

The present invention is directed to a cannula, attachable to an injection device comprising a needle entirely surrounded by an essentially cylindrical collapsible needle cover, in order to visually hide the entire needle during the whole procedure of administration by injection. The said needle cover provides an aperture for the needle through which the needle is forced into the injection site and is compressible against the injection site to such an extent that substantially the entire length of the needle is used for the injection. The needle cover will thereafter immediately reexpand while the needle is returned after the injection is accomplished. The needle and the needle aperture of the needle cover are always coaxially arranged in order to avoid unnecessary manipulations to bring the injection device into order for administration.

According to a preferred embodiment of the invention the collapsible needle cover comprises a resilient, cylindrical or vaguely conical sleeve made of a foamed polymer and is provided with an axial through hole forming an aperture for the needle. The sleeve can be provided with a flexible polyethylene film around its peripheral surface and the through hole can be provided with axial guiding surfaces. In an other embodiment the collapsible needle cover has a bellows like structure which is immediately penetrated by the needle to form an aperture during the injection.

The present invention is also directed to a method of administering a medicament by injection with the needle hidden from visual impression during the whole administration process, comprising a needle and a collapsible needle cover having the above-mentioned characteristics.

DETAILED DESCRIPTION OF THE INVENTION

FIG. 1 schematically shows a syringe according to the present invention with an attached resilient bellows formed needle cover immediately before administration.

Figures 1, 2:
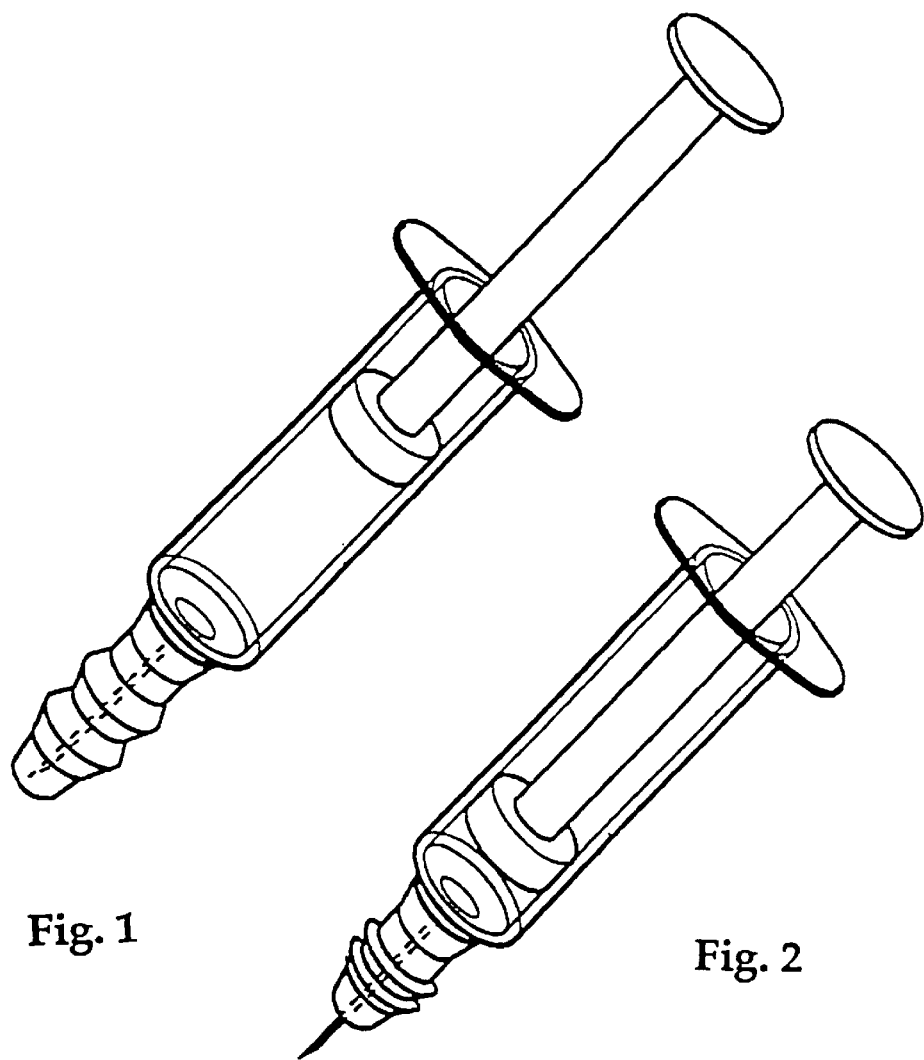
FIG. 2 shows the syringe according to FIG. 1 with the needle cover partially compressed during the administration.

The cannulas provided with collapsible needle covers according to the invention are possible to use with a large number of different injection devices, as schematically shown in FIGS. 1 and 2. The injection device may in its simplest form be a conventional syringe operated with a plunger and is prefilled with a liquid drug in the barrel or in an ampoule therein. However, the inventive cannulas are equally useful with more complicated injection devices of a pen-type, as the one for example disclosed in EP 0 298 067, intended for adjustable multi-dose administration from a reconstituted dual-chamber ampoule.

The cannulas will further comprise an attachment to the barrel or housing of the injection device which can be in the form of screw-threads, a conventional luer lock device or a snap-lock device of a conventional type. Moreover, it is provided with a needle holding part, also of a conventional type, to position the needle which typically is a standard needle, having for example a length of 8 or 12 mm, and is arranged to be in liquid communication with the drug in a conventional manner. It is an important feature of the present invention that the collapsible needle cover can be compressed as much as possible when pressing its front part against the injection site at the skin surface when penetrating the skin and administering the drug, so substantially the entire length of the needle will be used for injection. Otherwise an unnecessarily long needle must be used which will give rise to an inconvenient flow resistance during the injection.

Figures 3, 4, 5, 6, 7:
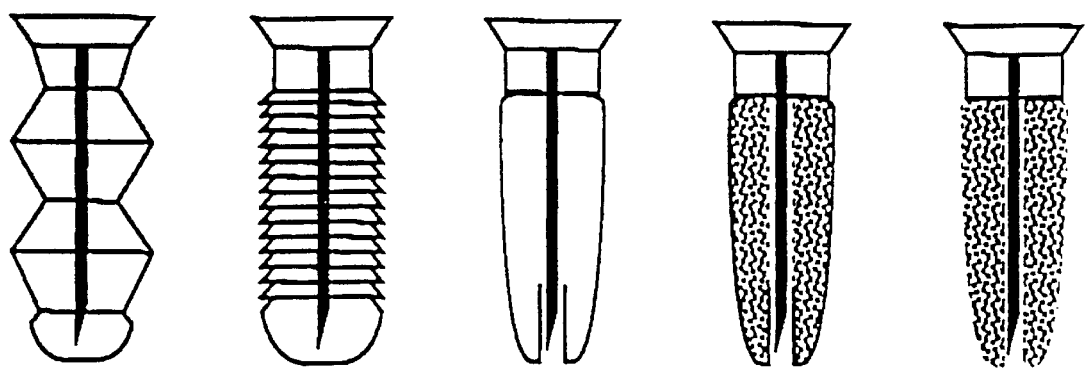
FIG. 3 shows a needle cover according to the present invention in the form of a resilient sleeve made of a foamed polymer.
FIG. 4 shows a device according to FIG. 3 provided with a flexible polyethylene film on its peripheral surface.
FIG. 5, shows a device according to FIG. 3 or 4 provided with a needle guiding surface
FIGS. 6 and 7 show collapsible needle covers with compressible bellows like structures.

In a preferred embodiment, as demonstrated in FIGS. 3 to 5, the cannula will comprise needle covers in the form of essentially cylindrical or vaguely conical resilient sleeves made of a foamed polymer of a very low density with elastomer properties, such as foamed low-density polyethene, in order to be highly compressible and yet immediately re-expandable after the injection is finished and while the needle is returned from point of injection in the body of the patient. The resilient sleeves are all provided with a centrally positioned, axially extended through hole, which precisely makes room for the needle when the pads are compressed. The front end of the through hole provides a needle aperture through which the needle is introduced into the injection site when compressing the resilient needle cover. It is important for a convenient injection performance that there is a minimum of frictional engagement between the needle and the sleeve during both the compression and the subsequent expansion of the sleeve. It can therefore be suitable to introduce a friction reducing agent in the though hole or on the peripheral surface of the needle. It is inevitable that the foamed polymer has a certain low internal friction, which preferably should be kept low in the inventive needle covers. It is also important that foamed polymeric material can be suitably sterilized, in spite of its porous material structure. The porous polymeric material may also be impregnated or filled with agents that contribute to an improved or facilitated injections, such as a sterilizing agent.

In a special embodiment the pad, see FIG. 4, can be provided with a flexible polyethylene film around its outer peripheral surface to obtain a smooth and non-porous contact surface to the skin which has a pleasant visual appearance. In another embodiment, as seen in FIG. 5, the front end of the through hole can be provided with an axially guiding surface to improve the precision of the injection. Such an arrangement is advantageous for securing a correct position of the needle, if the injection device is subjected to inadvertent transversal forces during the administration. The guiding surfaces are suitably made of the same material as the rest of the resilient sleeve and if a foamed polymer is used, they can be made by conventional surface melting.

If suitable, for the maintaining the integrity of the device, the front surface of the resilient sleeve can be equipped with a membrane which will be pierced by the needle when the device is compressed.

According to the alternative embodiments showed FIGS. 6 and 7, the cannula will comprise bellows like, essentially cylindrical, collapsible needle covers that also are compressible in a manner comparable to the said resilient sleeves, when the device is pressed against the injection site during the injection and thereafter immediately re-expanded while the needle is returned from the injection site after the injection is finished. The material used for the bellows like structure can typically be a elastic thermoplastic material with a high shaping capacity, such as sterilizable silicon latex. The needle will be enclosed within the bellows like structure before the injection and will retain its sterile integrity until the moment the cannula is compressed so it penetrates its enclosure and thereby forms an aperture for the needle at the injection site.

Injection devices comprising the inventive cannula, can be equipped with a protecting cap that is removed from the cannula before administration. After the injection is completed the cannula is removed and discarded or, if injection device is of a multi-dosage type, it is put aside, optionally with a new cannula attached.

An injection device can be delivered from the manufacturer integrated with the inventive cannula in its protective cap as an "all-in-one" kit, so there will be as few handling steps as possible for the patient.

In accordance with the present invention, it is also possible to let the collapsible needle cover be shaped to expand into a predetermined pleasant form when protective cap is removed to psychologically encourage an infant user to proceed with the injection.

The invention, as described in the foregoing, gives a surprisingly convenient, simple and cheap solution to the problem of hiding injection needles during the entire administration process of injecting a medicament for persons during that feel a strong aversion for injections with needles.

What is claimed is:

1. A cannula, attachable to an injection device containing a medicament administerable by injection, comprising a needle entirely surrounded by an essentially cylindrical, collapsible needle cover that visually hides the needle during the whole administration procedure and provides a needle aperture through which the needle is introduced into the injection site characterized in that the needle and the needle aperture of the needle cover are coaxially arranged and in that said needle cover is made collapsible in such a manner, that when it is compressed against the injection site, the needle is immediately introduced therein and substantially the entire length of the needle is used for the injection, whereupon it immediately reexpands while the needle is returned when the injection is accomplished and further characterized in that no molded end member is attached to the end of the needle cover.

2. A cannula according to claim 1, wherein the collapsible needle cover is in the form of a resilient sleeve made of a foamed polymer with an axially extended through hole forming an aperture for the needle.

3. A cannula according to claim 2, wherein the resilient sleeve is provided with a flexible polyethylene film around its peripheral surface.

4. A cannula according to claims 2, wherein the front end of through hole is provided with axially displaced guiding surfaces.

5. A cannula according to claims 2 characterized in that it is provided with protecting cap which when removed enables the resilient needle cover to expand into a predetermined shape.

6. A cannula according to claim 1, wherein the collapsible needle cover has a bellows like structure which is immediately penetrated by the needle to form an aperture during the injection.

7. A method of administering a medicament by injection with the needle hidden from visual impression during the whole administration procedure, wherein an injection device charged with the medicament and provided with a cannula according to any of claims 1, having a needle entirely surrounded of a collapsible needle cover, is compressed against the site of administration to such an extent so substantially the entire length of the needle is used for the injection, and whereby that the said collapsible needle cover immediately reexpands while the needle is returned after the injection is accomplished.

8. Use of a cannula according to claims 1 to 6 in the administration of a medicament by injection with the needle hidden from visual impression during the whole injection procedure.

9. A cannula, attachable to an injection device containing a medicament administrable by injection, comprising a needle surrounded by a collapsible needle cover that hides the needle during the administration procedure and provides a needle aperture through which the needle is introduced into the injection site, the collapsible needle cover is made of a foamed polymer material extending to its front end, without any molded end member attached at the front end, wherein when said collapsible needle cover is compressed against the injection site the needle is introduced therein and when the injection is accomplished the needle cover reexpands and the needle is returned.

10. A cannula according to claim 9, wherein the collapsible needle cover is a resilient sleeve made of a foamed polymer with an axially extended through hole that forms an aperture for the needle.

11. A cannula according to claim 10, wherein the resilient sleeve is provided with a flexible polyethylene film around its peripheral surface.

12. A cannula according to claim 10, wherein the font end of through hole is provided with axially displaced guiding surfaces.

13. A cannula according to claim 10 further comprising a protecting cap that when removed enables the resilient needle cover to expand into a predetermined shape.

14. A cannula according to claim 9, wherein the collapsible needle cover has a bellows like structure which is immediately penetrated by the needle to form an aperture during the injection.

15. A method of administering a medicament by injection with a needle hidden from visual impression during the administration procedure, wherein an injection device charged with the medicament is provided with a cannula according to claim 9, having a needle entirely surrounded with a collapsible needle cover, wherein when said collapsible needle cover is compressed against the injection site the needle is introduced therein and when the injection is accomplished the needle cover reexpands and the needle is returned.

16. A cannula, attachable to an injection device containing a medicament administrable by injection, comprising a needle surrounded by a collapsible needle cover made of a foamed polymer material having a melted polymer cover, which needle cover hides the needle during the administration procedure and provides a needle aperture through which the needle is introduced into the injection site, wherein when said collapsible needle cover is compressed against the injection site the needle is introduced therein and when the injection is accomplished the needle cover reexpands and the needle is returned, and wherein no tubular liner is between the needle and collapsible needle cover.

17. A cannula according to claim 16, wherein the collapsible needle cover is a resilient sleeve made of a foamed polymer with an axially extended through hole that forms an aperture for the needle.

18. A cannula according to claim 17, wherein the resilient sleeve is provided with a flexible polyethylene film around its peripheral surface.

19. A cannula according to claim 17, wherein the front end of through hole is provided with axially displaced guiding surfaces.

20. A cannula according to claim 16 further comprising a protecting cap that when removed enables the resilient needle cover to expand into a predetermined shape.

21. A cannula according to claim 16, wherein the collapsible needle cover has a bellows like structure which is immediately penetrated by the needle to form an aperture during the injection.

22. A method of administering a medicament by injection with a needle hidden from visual impression during the administration procedure, wherein an injection device charged with the medicament is provided with a cannula according to claim 16, having a needle surrounded in a collapsible needle cover, wherein when said collapsible needle cover is compressed against the injection site the needle is introduced therein and when the injection is accomplished the needle cover reexpands and the needle is returned.

23. A cannula, attachable to an injection device containing a medicament administrable by injection, comprising a needle surrounded by a collapsible needle cover that hides the needle during the administration procedure and provides a needle aperture through which the needle is introduced into the injection site, the needle and the needle aperture of the needle cover are coaxially arranged in that the needle aperture is covered by a needle pierceable membrane and in that said needle cover is made collapsible, wherein when said collapsible needle cover is compressed against the injection site, the needle is introduced therein, and when the injection is accomplished the needle cover reexpands and the needle is returned.

24. A cannula according to claim 23, where the collapsible needle cover is in the form of a resilient sleeve made of a foamed polymer with an axially extended through hole that forms an aperture for the needle.

25. A cannula according to claim 24, wherein the resilient sleeve is provided with a flexible polyethylene film around its peripheral surface.

26. A cannula according to claim 24, wherein the front end of through hole is provided with axially displaced guiding surfaces.

27. A cannula according to claim 24 further comprising a protecting cap which when removed enables the resilient needle cover to expand into a predetermined shape.

28. A cannula according to claim 23, wherein the collapsible needle cover has a bellows like structure which is immediately penetrated by the needle to form an aperture during the injection.

29. A method of administering a medicament by injection with a needle hidden from visual impression during the whole administration procedure wherein an injection device charged with the medicament is provided with a cannula according to claim 23, having a needle entirely surrounded in a collapsible needle cover, wherein when said collapsible needle cover is compressed against the injection site the needle is introduced therein and when the injection is accomplished the needle cover reexpands and the needle is returned.

* * * * *